United States Patent [19]
Webster, Jr.

[11] Patent Number: 5,827,278
[45] Date of Patent: Oct. 27, 1998

[54] DEFLECTABLE TIP ELECTRODE CATHETER WITH NYLON STIFFENER AND COMPRESSION COIL

[75] Inventor: Wilton W. Webster, Jr., Baldwin Park, Calif.

[73] Assignee: Cordis Webster, Inc., Baldwin Park, Calif.

[21] Appl. No.: 859,599

[22] Filed: May 20, 1997

[51] Int. Cl.⁶ .................................................. A61B 17/36
[52] U.S. Cl. ............................ 606/41; 607/101; 607/122; 600/374
[58] Field of Search .................................. 604/95, 21, 22; 600/374; 606/41, 45, 46; 607/100–102, 122

[56] References Cited

U.S. PATENT DOCUMENTS

| | | |
|---|---|---|
| 3,625,200 | 12/1971 | Muller . |
| 4,921,482 | 5/1990 | Hammerslag et al. . |
| 4,998,916 | 3/1991 | Hammerslag et al. . |
| 5,037,391 | 8/1991 | Hammerslag et al. . |
| 5,069,674 | 12/1991 | Fearnot et al. . |
| 5,108,368 | 4/1992 | Hammerslag et al. . |
| 5,184,621 | 2/1993 | Vogel et al. . |
| 5,203,772 | 4/1993 | Hammerslag et al. . |
| 5,211,636 | 5/1993 | Mische . |
| 5,246,009 | 9/1993 | Adams . |
| 5,308,324 | 5/1994 | Hammerslag et al. . |
| 5,318,525 | 6/1994 | West et al. ................................ 604/95 |
| 5,329,923 | 7/1994 | Lundquist . |
| 5,345,945 | 9/1994 | Hodgson et al. . |
| 5,368,564 | 11/1994 | Savage . |
| 5,376,083 | 12/1994 | Mische . |
| 5,383,467 | 1/1995 | Auer et al. . |
| 5,397,304 | 3/1995 | Truckai . |
| 5,397,321 | 3/1995 | Houser et al. ............................ 606/41 |
| 5,409,453 | 4/1995 | Lundquist et al. . |
| 5,431,168 | 7/1995 | Webster . |
| 5,439,000 | 8/1995 | Gunderson et al. . |
| 5,472,017 | 12/1995 | Kovalcheck . |
| 5,477,856 | 12/1995 | Lundquist . |
| 5,478,330 | 12/1995 | Imran et al. ............................ 604/282 |
| 5,480,382 | 1/1996 | Hammerslag et al. . |
| 5,497,783 | 3/1996 | Urick et al. . |
| 5,507,301 | 4/1996 | Wasicek et al. . |
| 5,507,725 | 4/1996 | Savage et al. . |
| 5,522,875 | 6/1996 | Gates et al. . |
| 5,527,292 | 6/1996 | Adams et al. . |
| 5,549,542 | 8/1996 | Kovalcheck . |
| 5,558,093 | 9/1996 | Pomeranz . |
| 5,562,275 | 10/1996 | Weissenfluh et al. . |
| 5,562,619 | 10/1996 | Mirarchi et al. ........................... 604/95 |
| 5,571,073 | 11/1996 | Castillo . |
| 5,571,085 | 11/1996 | Accisano, III . |
| 5,571,087 | 11/1996 | Ressemann et al. . |
| 5,573,010 | 11/1996 | Pflugbeil . |
| 5,573,520 | 11/1996 | Schwartz et al. . |
| 5,681,280 | 10/1997 | Rusk et al. . |

Primary Examiner—Jennifer Bahr
Assistant Examiner—Roy D. Gibson
Attorney, Agent, or Firm—Christie, Parker & Hale, LLP

[57] ABSTRACT

A deflectable tip catheter includes an elongated catheter body, a tip section carrying electrodes at the distal end of the catheter body and a control handle at the proximal end of the catheter body. The catheter body has a central lumen and the tip section has a pair of off axis lumens in communication with the central lumen of the catheter body. A compression coil is disposed in the central lumen of the catheter body and is fixedly attached at its proximal and distal ends to the proximal and distal ends of the catheter body by means of glue joints. A tunnel, formed by a short piece of tubing, is provided through each glue joint. A puller wire extends from the control handle, through the compression coil and into one off axis lumen of the tip section and is attached at is distal end to the wall of the tip section. Electrode lead wires pass from the central handle through the tunnels and central lumen of the catheter body and into the other off axis lumen of the tip section and are electrically connected to separate electrodes.

9 Claims, 3 Drawing Sheets

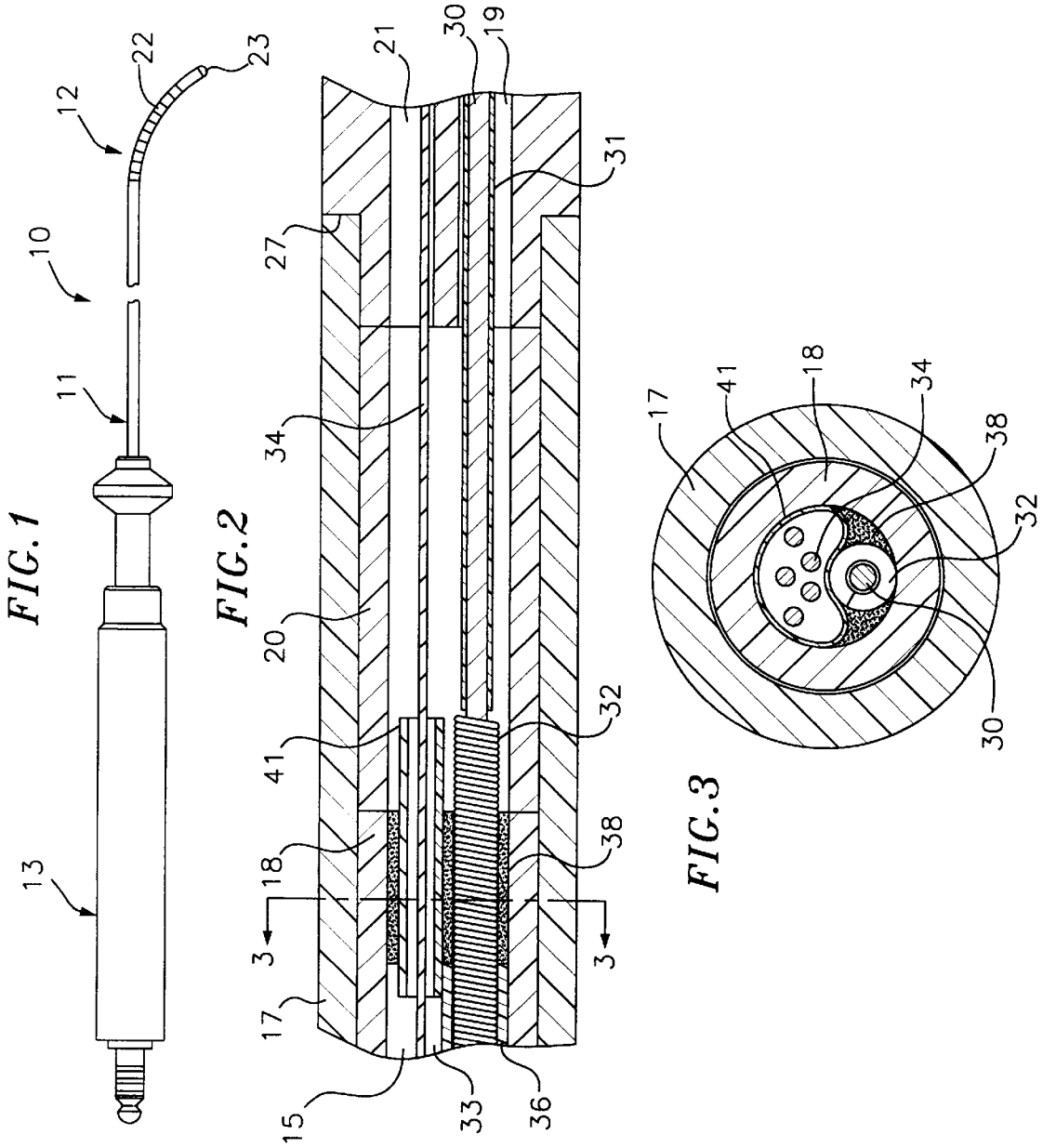

DEFLECTABLE TIP ELECTRODE CATHETER WITH NYLON STIFFENER AND COMPRESSION COIL

FIELD OF THE INVENTION

This invention relates to electrode catheters having a steerable or deflectable tip and more particularly to a deflectable tip electrode catheter having an elongated single lumen catheter body containing a compression coil which is resistant to compressive forces.

BACKGROUND OF THE INVENTION

Steerable or deflectable tip cardiovascular catheters are useful in many applications, being a marked improvement over catheters with fixed tip curves. They are especially useful in the field of electrophysiology for performing radio frequency ablation of abnormal electrical pathways in the heart.

There are presently several useful designs of steerable tip catheters. One such steerable tip catheter is described in U.S. Reissue Pat. No. 34,502 which is incorporated herein by reference. The catheter described has an elongated catheter body and tip portion which can be deflected into a semi-circle in one direction. In addition, the catheter body and tip portion can be rotated. By tip deflection, catheter rotation and catheter translation, i.e., lengthwise movement of the catheter, contact of the tip portion with most areas of a heart chamber may be made.

In the catheter described in Reissue U.S. Pat. No. 34,502, the deflectable tip section has two opposing offset lumens, one for electrode lead wires and one for a puller wire. The puller wire is disposed within a tiny Teflon® tube or sheath that extends the entire length of the catheter tip and body. In the catheter body, the puller wire within the Teflon sheath and the lead wires extend centrally within a nylon stiffener tube. The lumen of the nylon tube is just big enough to pass the puller wire with its Teflon sheath and the lead wires, thereby maintaining the puller wire in an substantially axial or central position. This central puller wire, when pulled by the control handle at the proximal end of the body, deflects the tip and also compresses the catheter body including the nylon stiffener. Because the puller wire is almost exactly on the axis of the catheter body, there is almost no bending moment and hence almost no bending of the catheter body. Even so, compression of the catheter body does cause a certain waviness of the body, which results in a slight loss of performance.

The open lumen catheter described in U.S. Pat. No. 5,431,168 has a compression coil deployed in one of three off-axis lumens in a braided catheter body. In this catheter, the compressive forces on the catheter body when the puller wire is manipulated to deflect the tip is transferred to the compression coil. This is done by gluing the distal and proximal ends of the compression coil to the ends of the catheter body using a sufficient amount of an appropriate glue to effect shear joints that are stronger than the forces created by the puller wire. This design requires a dedicated compression coil lumen. Because the puller wire and compression coil are not located on the axis of the catheter body, manipulation of the catheter is compromised somewhat in order to achieve an open lumen for irrigation.

SUMMARY OF THE INVENTION

The present invention provides a single lumen deflectable tip electrode catheter having a substantially non-compressive catheter body. The catheter comprises an elongated catheter body, a control handle at the proximal end of the catheter body and a deflectable tip section at the distal end of the catheter body which carries one or more electrodes. The catheter body comprises a central, i.e., axial, lumen. The tip section comprises at least one, and preferably at least two off-axis lumens which are in communication with the central lumen of the catheter body.

A puller wire extends through the central lumen of the catheter body and into one off-axis lumen of the catheter tip section, the distal end of the puller wire being anchored to the side wall of the tip section, preferably near the distal end of the tip section. The puller wire preferably comprises a lubricious Teflon sheath to increase sidability of the puller wire within the catheter body and tip section.

In the central lumen of the catheter body, there is provided a compression coil in surrounding relation to the puller wire. The compression coil is flexible, i.e., bendable, but is substantially non-compressible. The diameter of the compression coil is sufficiently less than the diameter of the central lumen of the catheter body to provide a space or gap through which electrode wires may pass. The proximal end of the compression coil is fixedly attached to the proximal end of the catheter body by a first glue joint. The distal end of the compression coil is fixedly attached to the distal end of the catheter body or proximal end of the tip section by a second glue joint. First and second tunnels preferably made from short pieces of non-conductive tubing, e.g., polyamide tubing, extend through the first and second glue joints. The tunnels are sufficiently large to allow the passage of electrode lead wires therethrough. In a preferred embodiment, the outer surface of the compression coil between the glue joints is covered by a non-conductive sleeve, preferably polyamide tubing. Preferably the sleeve overlaps the tunnels.

BRIEF DESCRIPTION OF THE DRAWINGS

FIG. 1 is a side view of a preferred electrode catheter constructed in accordance with the present invention.

FIG. 2 is a fragmentary longitudinal, cross-sectional side view of the catheter of FIG. 1 showing the distal end of the catheter body and proximal end of the tip section in cross-section except for the compression coil and tunnel.

FIG. 3 is a transverse cross-sectional view of the catheter body shown in FIG. 2 taken along line 3—3.

DETAILED DESCRIPTION

Figure 5A:
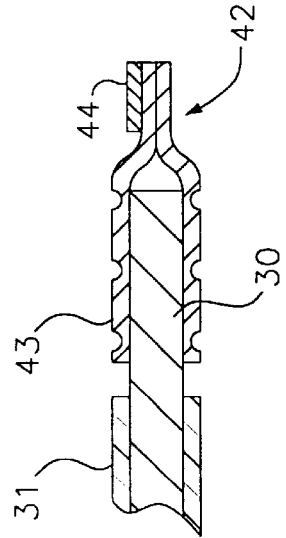
FIGS. 5a and 5b are top and side cross-sectional views of a preferred puller wire anchor.

A particularly preferred electrode catheter constructed in accordance with the present invention is shown in FIGS. 1–5. The electrode catheter 10 comprises an elongated catheter body 11 having proximal and distal ends, a catheter tip section 12 at the distal end of the catheter body 11 and a control handle 13 at the proximal end of the catheter body 11.

The catheter body 11 comprises an elongated tubular construction having a single, central or axial, lumen 15. The catheter body 11 is flexible i.e. bendable, but substantially non-compressible along its length. The catheter body 11 may be of any suitable construction and made of any suitable material. A presently preferred construction comprises an outer polyurethane wall 17 containing a braided stainless steel mesh. Lining the interior of the polyurethane wall 17 is a nylon stiffening tube 18, the interior of which forms the central lumen 15. The nylon stiffening tube 18 is fixedly attached to the outer polyurethane wall 17, typically at its proximal end by polyurethane glue or the like.

The length and diameter of the catheter body 11 are not critical and may vary according to the application. For the electrode catheter 10 shown in the accompanying drawings, a length of about 48 inches, an outer diameter of about 0.09 inch in an inner lumen diameter of about 0.035 inch is presently preferred.

The catheter tip section 12 comprises a short section of flexible tubing 16 having a pair of non-overlapping, side-by-side off-axis lumens 19 and 21. The catheter tip section 12 may be made of any suitable material and is preferably more flexible than the catheter body. A preferred material for the catheter tip is polyurethane having a hardness of Shore D55. The catheter tip section 12 preferably comprises a braided stainless steel mesh similar to that of the catheter body 11.

The diameter of the catheter tip section 12 is not critical, but is preferably about the same as, or slightly smaller, than diameter of the catheter body 11. The length of the catheter tip section 12 is likewise not critical. In the embodiment shown, the length of the catheter tip section 12 is about 3 inches and the diameter is about 0.09 inch.

The catheter tip section 12 carries a plurality of a electrodes 22. The electrodes 22 are in the form metal rings, the outer diameter of the electrodes 22 being about the same as the outer diameter of the flexible tubing 16 of the tip section so that the electrodes 22 form a smooth, continuous surface with that outer of the surface of the flexible tubing 16. Alternatively, the electrodes 22 may have an outer diameter slightly larger than the diameter of the flexible tubing 16 so that the electrodes 22 protrude slightly from the surface of the flexible tubing 16. A rounded end electrode 23 is positioned at the distal end of the catheter tip section 12. The longitudinal length and spacing of the ring electrodes are not critical. A longitudinal length of about 1 mm and a spacing from about 2 mm to about 5 mm are presently preferred.

A preferred means for attaching the catheter tip section 12 to the catheter body 11 is shown in FIG. 2. The proximal end of the catheter tip section 12 comprises an outer circumferential notch 27 which receives the inner surface of the outer wall 17 of the catheter body. In the arrangement shown, a Teflon® spacer 20 having about the same inner and outer diameters as the nylon stiffening tube 18 lies between the distal end of the nylon stiffening tube 18 and the proximal end of the catheter tip section 12.

A puller wire 30, preferably made of stainless steel, Nitinol, Kevlor, carbon fiber or the like, extends from the control handle 13 through the central lumen 15 of the catheter body and into the first lumen 19 of the catheter tip section 12. The puller wire 30 extends into the first lumen 19 of the catheter tip section 12 to a position near the distal end of the catheter tip section 12 and is fixedly attached to the wall of the flexible tubing 16. The puller wire 30 is preferably coated with a Teflon coating or the like for lubricity. Within the Teflon® spacer and the catheter tip section 12, the puller wire 30 lies within a Teflon® sheath 31.

Within the catheter body 11, the puller wire 30 extends through a compression coil 32. The compression coil is made of a suitable metal, e.g., stainless steel, which is tightly wound on itself to provide flexibility, i.e., bending, but to resist compression. The compression coil 32 preferably has a length a little longer than the length of the nylon stiffening tube 18 and extends into the Teflon® spacer 20. The inner diameter of the compression coil 32 is slightly larger than the outer diameter of the puller wire 30. This allows the puller wire 30 to slide easily through the compression coil 32. The inner diameter of the central lumen 15 and the outer diameter of the compression coil 32 are selected to provide a small gap or space 33 between the compression coil 32 and the inner surface of the nylon stiffening tube 18 which forms the central lumen 15 for passage of electrode lead wires 34.

The outer surface of the compression coil 32 is covered by a flexible, non-conductive sheath 36 to prevent contact between the electrode lead wires 34 in the gap 33 and the compression coil 32. A non-conductive sheath 36 made of polyamide tubing is presently preferred.

The compression coil 32 is fixedly attached to the proximal and distal ends of the nylon stiffening tube 18 by glue joints 38 preferably made from polyurethane glue or the like. At each glue joint 38, the non-conductive sheath 36 surrounding the compression coil 32 is removed so that the glue contacts the compression coil 32 directly. The glue may be applied through a syringe or the like to the outer circumference of the end of the compression coil. Glue applied to such a location seeps inwardly between the compression coil and the wall forming the lumen. Upon drying, the glue joint is formed. Alternatively, the glue may be applied by means of a syringe or the like through a hole between the outer surface of the catheter body and the lumen. Such a hole may be formed for example by a needle or the like which punctures the catheter body wall and is heated sufficiently to form a permanent hole. The glue is introduced through the hole to the outer surface of the compression coil and wicks around the outer circumference to form a glue joint about the entire circumference of the compression coil.

If the latter method is used, it is understood that the distal end of the compression coil could be located in the proximal portion of the catheter tip section rather than from at the distal end of the catheter body. Such an embodiment provides added support to the juncture of the catheter body and catheter tip section.

A tunnel is formed through each glue joint 38 by means of a small piece of non-conductive tubing 41 preferably made of polyamide, positioned adjacent the compression coil 32 within the central lumen 15. The length of the tubing 41 is sufficient to extend entirely through the glue joint 38 and to overlap the non-conductive sheath 36 around the compression coil 32. The tubing 41 may be generally circular in cross section or may be deformed to have, for example, a generally C-shaped cross-sectional shape. The interior cross-sectional area of the tubing 41 is sufficient to allow electrode lead wires 34 to pass therethrough. The Tubing 41 which forms a tunnel through the distal glue joint 38 preferably extends a short distance into the Teflon® spacer 20.

In an exemplary embodiment wherein the outer diameter of the catheter body 11 is 0.09 inch, the outer diameter of the puller wire 30 is about 0.007 inch to about 0.010 inch, the thickness of the Teflon coating 31 around the puller wire 30 is about 0.0001 to about 0.0002 inch, the inner and outer diameter of the compression coil 32 is 0.009 inch and 0.018 inch respectively, the thickness of the sheath 36 surrounding the compression coil 32 is about 0.001 inch, the inner diameter of the central lumen 15 is about 0.035, and the inner diameter of the tunnels is from about 0.015 to about 0.020 inch. It is understood that all of these dimensions may vary as desired.

Figure 5B:
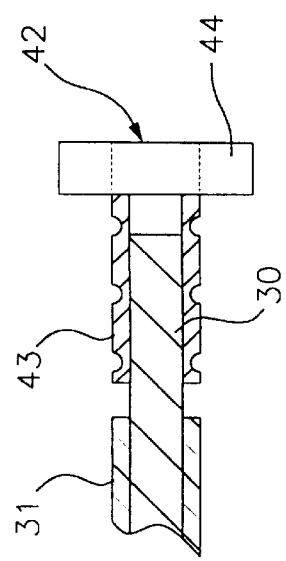
Figure 4:
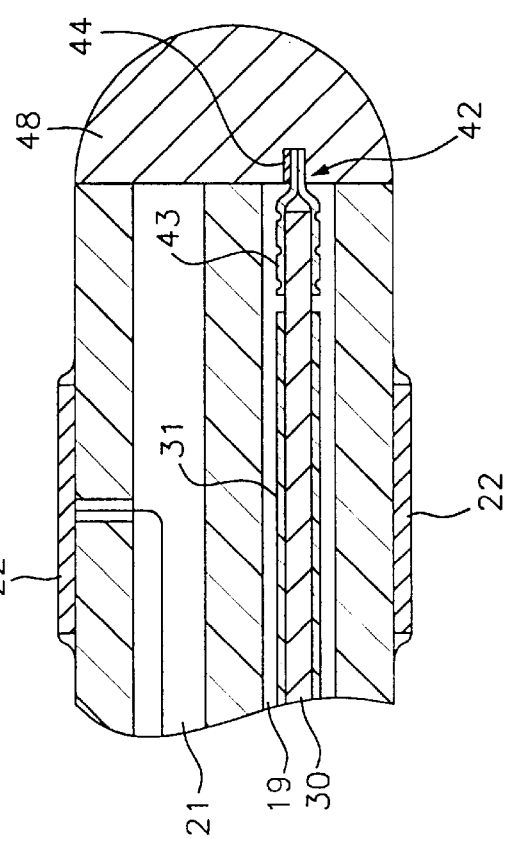
FIG. 4 is a cross-sectional view of a portion of the catheter tip section showing a preferred means for anchoring the puller wire.

A preferred means for attaching the puller wire 30 to the tubing 16 of the catheter tip section 12 is shown in FIGS. 4 and 5. A T-shaped anchor 42 is formed which comprises a short piece of tubular stainless steel 43, e.g. hypodermic stock, which is fitted over the distal end of the puller wire 30 and crimped to fixedly secure it to the puller wire 30. The distal end of the tubular stainless steel 43 is fixedly attached e.g. by welding, to a stainless steel cross-piece 44 such as stainless steel ribbon or the like. The cross-piece 44 sits in a notch 46 in a wall of the flexible tubing 16 which extends into the lumen 19. This provides a small opening through the wall of the flexible tubing 16 into the lumen 19. The stainless steel cross-piece 44 is larger than the opening and, therefore, cannot be pulled through the opening. The portion of the notch 46 not filled by the cross-piece 44 is filled with glue 47 or the like, preferably a polyurethane glue, which is harder than the material of the flexible tubing 16. Rough edges, if any, of the cross-piece 44 are polished to provide a smooth, continuous surface with the outer surface of the flexible tubing 16.

Figure 6:
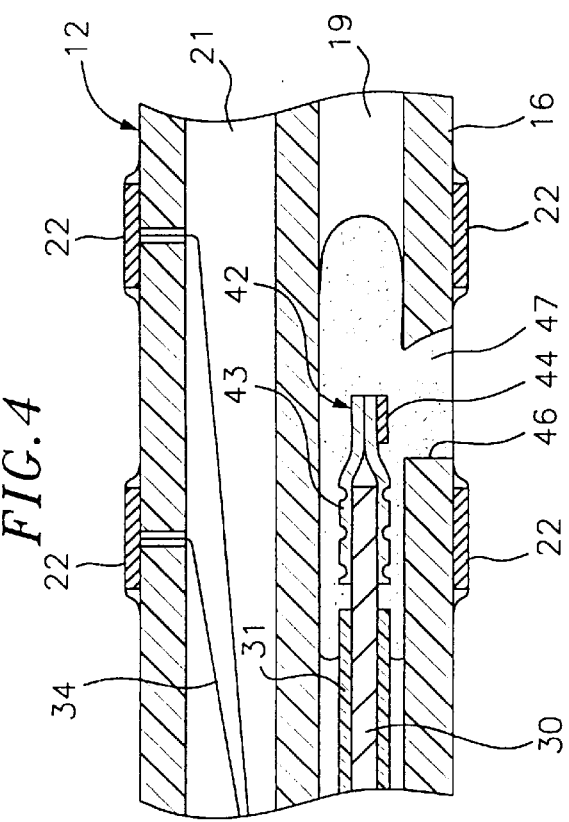
FIG. 6 is a cross-sectional view of a portion of the catheter tip section showing another preferred means for anchoring the puller wire.

With reference to FIG. 6, there is shown an alternate embodiment wherein the puller wire 30 extends to the distal end of the lumen 19 with the cross-piece 44 of anchor 42 lying beyond the end of lumen 19. The cross-piece 44 is fixed at this position by a polyurethane cap 48 which also seals the distal end of the catheter tip section 12. Because the cross-piece 44 is larger than the diameter of the lumen 19, the anchor 42 cannot be pulled back into the lumen 19 when the tip section 12 is deflected. This alternative anchoring arrangement is useful when there is no tip electrode. If a tip electrode is present, the puller wire 30 may be fixedly attached to the tip electrode or anchored through the side wall of the tip section 12 as shown in FIG. 4.

Figure 7:
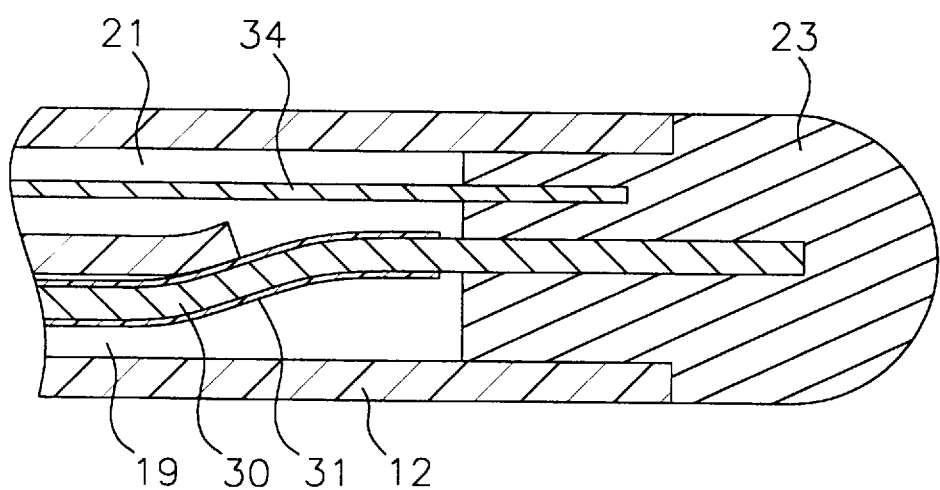
FIG. 7 is a cross-sectional view of the distal portion of a catheter tip section comprising a tip electrode showing yet another preferred means for anchoring the puller wire.

With reference to FIG. 7, there is shown yet another embodiment wherein the tip section 12 carries a tip electrode 23. The distal end of the puller wire 30 extends into a hole in the tip electrode 23 is attached thereto, e.g., by soldering. The hole in the tip electrode 23 may be axial as shown or off axis as desired.

The electrode lead wire 34 likewise extends into a hole in the tip electrode 23 and is electrically bonded, e.g., by soldering thereto. It is to be understood that any suitable means for fixedly attaching the puller wire 30 and electrode lead wire 34 to the tip electrode 23 may be used as desired.

Electrode lead wires 34 extend from the control handle 13 through the first tunnel, i.e., tubing 41, at the proximal end of the catheter body 11, through the space 33 between the compression coil 32 and the inner surface of the nylon stiffening tube 18 forming central lumen 15, through the second tunnel, i.e., tubing 41, at the distal end of the catheter body 11 and into lumen 19 in the catheter tip section 12. The lead wires 34 are attached to the electrodes 22 by any conventional technique. In a preferred embodiment, connection of a lead wire 34 to an electrode 22 is accomplished by first making a small hole through the wall of the catheter tip section and into the second lumen 21. Such a hole may be created, for example, by inserting a needle through the tip section wall and heating the needle sufficiently to form a permanent hole. A lead wire 34 is then drawn through the hole by using a micro hook or the like. The end of the lead wire 34 is then stripped of any coating and soldered or welded to the underside of the electrode 22 which is then slid into position over the hole and fixed in place with polyurethane glue or the like.

Longitudinal movement of the puller wire 30 relative to the catheter body 11 which results in deflection of the catheter tip section 12 is accomplished by manipulation of a suitable control handle 13. A particularly preferred control handle useful in the present invention is disclosed in U.S. Pat. Re/34,502 which is incorporated herein by reference.

The preceding description has been presented with reference to presently preferred embodiments of the invention. Workers skilled in the art and technology to which this invention pertains will appreciate that alterations and changes in the described structure may be practiced without meaningfully departing from the principal, spirit and scope of this invention.

Accordingly, the foregoing description should not be read as pertaining only to the precise structures described and illustrated in the accompanying drawings, but rather should be read consistent with and as support to the following claims which are to have their fullest and fair scope.

I claim:

1. A deflectable electrode catheter comprising:

a catheter body having proximal and distal ends, a central axis and a central lumen therethrough;

a catheter tip section at the distal end of the catheter body having an off-axis lumen in communication with the central lumen of the catheter body, said tip section carrying at least one electrode;

a puller wire having proximal and distal ends extending through the central lumen of the catheter body and into the off-axis lumen of the catheter tip section, the distal end of the puller wire being fixedly attached to the tip section at a selected location;

a compression coil having proximal and distal ends extending through the central lumen of the catheter body in surrounding relation to the puller wire, said compression coil having an outer diameter less than the inner diameter of the central lumen of the catheter body sufficient to form a space through which electrode lead wires may extend;

a first glue joint fixedly attaching the proximal end of the compression coil to the proximal end of the catheter body, said first glue joint comprising a first tunnel through which electrode lead wires may pass;

a second glue joint fixedly attaching the distal end of the compression coil to the distal end of the catheter body, said second glue joint comprising a second tunnel through which electrode lead wires may pass;

a control handle comprising means, connected to the puller wire, for reversibly moving the puller wire in a proximal direction relative to the catheter body to thereby cause deflection of the tip section; and at least one electrode lead wire, each of said at least one electrode lead wire having proximal and distal ends and being associated with one of said at least one electrode carried by the tip section, and each of said at least one electrode lead wire extending through the central lumen of the catheter body in the space between the compression coil and the wall of the central lumen, through each of the first and second tunnels and into a lumen in the tip section, the distal end of each of said at least one electrode lead wire being electrically connected to its associated electrode.

2. A deflectable electrode catheter as claimed in claim 1 wherein the catheter body comprises a nylon stiffening tube, the hollow interior of which forms the central lumen.

3. A deflectable electrode catheter as claimed in claim 1 further comprising a flexible non-conductive sleeve in surrounding relation to the compression coil.

4. A deflectable electrode catheter as claimed in claim 3 wherein the non-conductive sleeve is made of polyamide.

5. A deflectable electrode catheter as claimed in claim 1 wherein at least one of the first and second tunnels are formed by short pieces of non-conductive tubing.

6. A deflectable electrode catheter comprising:

a catheter body having proximal and distal ends, a central axis and a central lumen therethrough;

a catheter tip section at the distal end of the catheter body having an off-axis lumen in communication with the central lumen of the catheter body, said tip section carrying at least one electrode;

a puller wire having proximal and distal ends extending through the central lumen of the catheter body and into the off-axis lumen of the catheter tip section, the distal end of the puller wire being fixedly attached to the tip section at a selected location;

a compression coil having proximal and distal ends extending through the central lumen of the catheter body in surrounding relation to the puller wire, said compression coil having an outer diameter less than the inner diameter of the central lumen of the catheter body sufficient to form a space through which electrode lead wires may extend;

a non-conductive sleeve in surrounding relation to the compression coil;

a first glue joint fixedly attaching the proximal end of the compression coil to the proximal end of the catheter body;

a first tunnel in the first glue joint through which electrode lead wires may pass formed by a short piece of non conductive tubing;

a second glue joint fixedly attaching the distal end of the compression coil to the distal end of the catheter body;

a second tunnel in the second glue joint through which electrode lead wires may pass formed by a short piece of non-conductive tubing;

a control handle comprising means, connected to the puller wire, for reversibly moving the puller wire in a proximal direction relative to the catheter body to thereby cause deflection of the tip section; and at least one electrode lead wire each of said at least one electrode lead wire having proximal and distal ends and being associated with one of said at least one electrode carried by the tip section, and each of said at least one electrode lead wire extending through the central lumen of the catheter body in the space between the compression coil and the wall of the central lumen, through each of the first and second tunnels and into a lumen in the tip section, the distal end of each of said at least one electrode lead wire being electrically connected to its associated electrode.

7. A deflectable electrode catheter as claimed in claim 6 wherein the catheter body comprises a nylon stiffening tube, the hollow interior of which forms the central lumen.

8. A deflectable electrode catheter as claimed in claim 6 wherein the non-conductive sleeve is made of polyamide.

9. A deflectable electrode catheter as claimed in claim 6 wherein the short pieces of non-conductive tubing are made of polyamide.

* * * * *